(12) United States Patent
Karlsson et al.

(10) Patent No.: US 7,050,544 B2
(45) Date of Patent: May 23, 2006

(54) X-RAY DIAGNOSTIC DEVICE WITH FILTERS AND A BEAM SIGHTING MIRROR MOUNTED ON A COMMON ROTATABLE DISK

(75) Inventors: Stefan Karlsson, Sollentuna (SE); Rob Olthoff, Spånga (SE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/920,815

(22) Filed: Aug. 18, 2004

(65) Prior Publication Data

US 2005/0063517 A1    Mar. 24, 2005

(30) Foreign Application Priority Data

Aug. 18, 2003  (DE) ................. 103 37 931

(51) Int. Cl.
*G21K 1/04*  (2006.01)
(52) U.S. Cl. .............. 378/158; 378/148; 378/160; 378/206
(58) Field of Classification Search ........... 250/236, 250/237, 491.1, 233; 378/37, 157, 206, 148, 378/158, 160
See application file for complete search history.

(56) References Cited

U.S. PATENT DOCUMENTS

| 2,556,866 | A | * | 6/1951 | Bucky ........................ 378/98 |
| 4,167,675 | A | | 9/1979 | Stödberg et al. |
| 4,627,089 | A | * | 12/1986 | Menor et al. ............... 378/157 |
| 4,744,099 | A | | 5/1988 | Huettenrausch et al. |
| 4,825,076 | A | * | 4/1989 | Shields ....................... 250/343 |
| 6,036,362 | A | * | 3/2000 | Schmitt ...................... 378/206 |
| 6,305,842 | B1 | * | 10/2001 | Kunert ........................ 378/206 |
| 6,898,271 | B1 | * | 5/2005 | Akutsu et al. .............. 378/157 |

* cited by examiner

*Primary Examiner*—Edward J. Glick
*Assistant Examiner*—Anastasia Midkiff
(74) *Attorney, Agent, or Firm*—Schiff Hardin LLP

(57) ABSTRACT

An X-ray diagnostic device has an X-ray tube and a diaphragm housing in which diaphragm plates for limiting an X-ray field are contained, as are a lamp and a mirror. The lamp and mirror are configured so that, when the lamp is on, the light therefrom is reflected by the mirror so that the reflected ray field coincides with the hypothetical X-ray field. At least one filter for filtering the X-rays is disposed in the diaphragm housing. The mirror and the filter or filters are attached to a single disk that rotates around an axis such that either the mirror or a filter is within the hypothetical X-ray field.

2 Claims, 2 Drawing Sheets

X-RAY DIAGNOSTIC DEVICE WITH FILTERS AND A BEAM SIGHTING MIRROR MOUNTED ON A COMMON ROTATABLE DISK

BACKGROUND OF THE INVENTION

1. Field of the Invention

The present invention relates to an X-ray diagnostic device of the type having an X-ray tube and a diaphragm housing in which diaphragm plates or blades for limiting an X-ray field are disposed, and in which a lamp and mirror are disposed such that, when the lamp is illuminated, the light is reflected by the mirror so that the reflected light ray field substantially coincides with the hypothetical (expected) X-ray field, and in which at least one filter for filtering the X-rays also is disposed.

2. Description of the Prior Art

An X-ray diagnostic device with an X-ray tube and a diaphragm housing of the above type is known from a mammography device commercially available from Siemens, as described in a brochure under the name "MAM-MOMAT 3000 NOVA."

Prior to an exposure, the lamp is turned on, and the light is reflected as described above by the mirror that is placed in the hypothetical X-ray field, and consequently a light field is directed onto a subject that is to be examined. This light field is limited by the above-mentioned diaphragms, so that a desired region of the subject is illuminated by the light field. A diaphragm, lamp, and mirror of the kind described above are described in detail in U.S. Pat. No. 4,167,675. After the light field is set, the mirror must be removed from the hypothetical X-ray field, which is accomplished by a motor-controlled mechanical arrangement in known fashion.

One of, for example, three filters to filter the X-radiation must be selected prior to an X-ray exposure. The filters are attached to a disk, for example, the disk being rotatable around its own axis by means of a motor, so the selected filter is rotated into a position within the hypothetical X-ray field. A configuration of this kind is described in German OS 33 39 775.

The above-described arrangements require separate mechanical configurations, namely separate fastenings, bearings, motors, and separate control mechanisms, which requires space and is very expensive.

SUMMARY OF THE INVENTION

An object of the present invention is based to provide an X-ray diagnostic device of the above type in which the arrangement for the mirror and filter or filters forms a relatively space-efficient, simple and inexpensive unit.

This object is inventively achieved by an x-ray diagnostic device of the above type wherein the mirror and filter or filters are attached to a disk that rotates around an axis such that either the mirror or a filter lies within the hypothetical X-ray field. With the mirror and filters placed on one and the same disk, only one mounting disk, one motor for rotating the disk, and one common control mechanism for the mirror and filters are required. The invention reduces the number of components and at the same time achieves a simplification of the setting of the mirror and filters in the hypothetical X-ray field.

In an embodiment of the inventive X-ray diagnostic device, the disk is round and at least a portion of its periphery is provided with teeth that interact with a motor-driven transmission. The disk for the filters and the mirror, together with the drive mechanism for the disk, thus form an extraordinarily compact unit, given that the motor can be engaged on the side of the disk.

DESCRIPTION OF THE PREFERRED EMBODIMENTS

Figure 1:
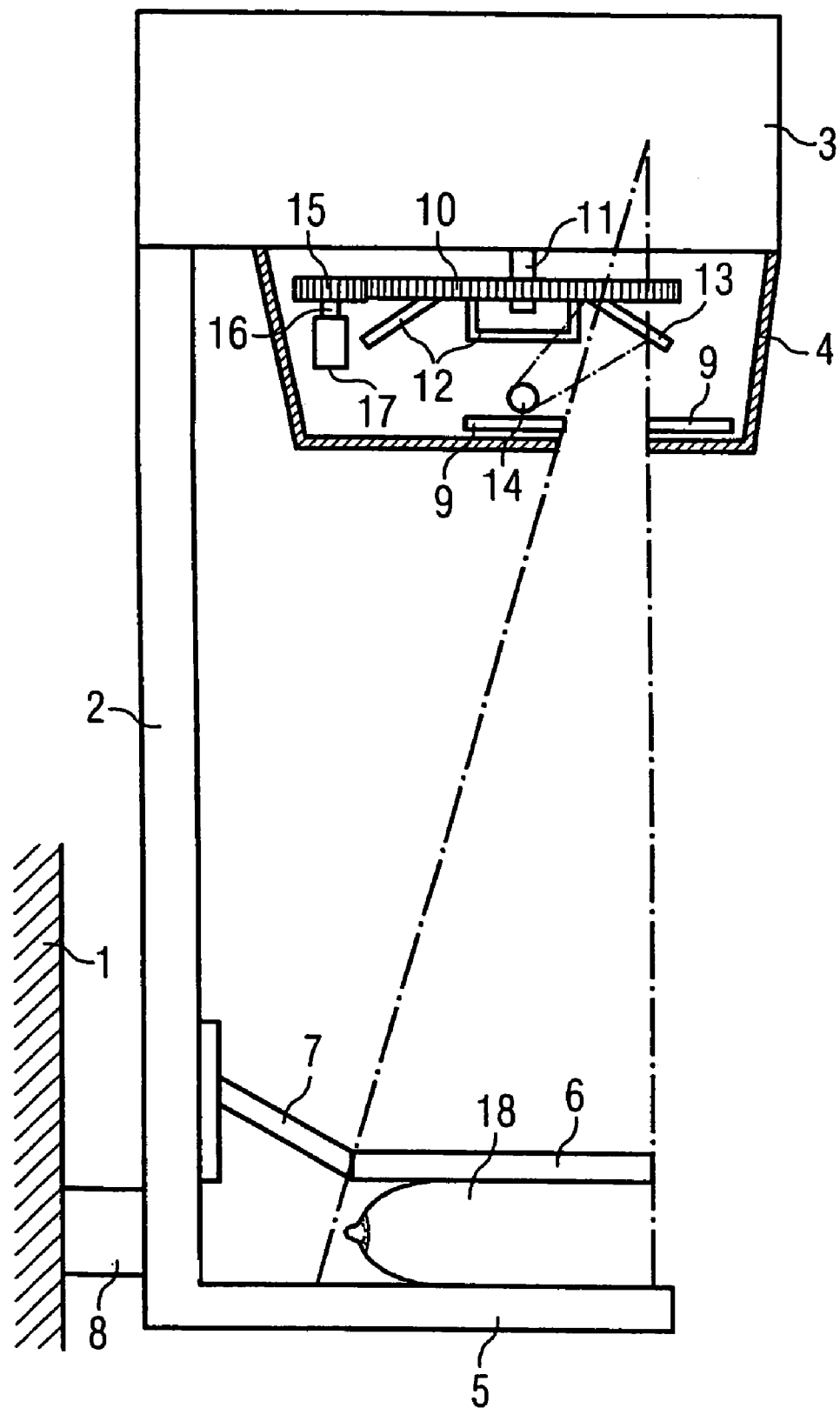
FIG. 1 is a side view, partly in section of an inventive X-ray device.

FIG. 1 is a side view of an X-ray diagnostic device for mammography examinations for which a part of a device stand 1 is shown that supports an arm 2 for an X-ray tube 3 with a diaphragm housing 4 and a subject table 5. Disposed between the X-ray tube 3 and diaphragm housing 4 and the subject table 5, is a compression plate 6, which is connected to the arm 2 by a bracket 7 and is movable along the arm 2. The arm 2 is connected in rotating fashion to the device stand 1 by a horizontal shaft 8.

The diaphragm housing 4, which is shown in FIG. 1 in cross-section, contains, among other things, diaphragm plates 9 for limiting an X-ray field and a disk 10, described in detail below, which is connected to a shaft 11 in rotating fashion, with the shaft 11 mounted at the interior wall of the diaphragm housing 4. The disk 10 carries a number of filters 12 for filtering the X-radiation and a mirror 13. The diaphragm housing 4 further contains a lamp 14, described in detail below, which is fastened to the interior wall of the diaphragm housing 4. The disk 10 is round and its periphery is provided with teeth 19 (see FIG. 2) that engage the teeth of a spur gear 15, which is connected with a motor 17 by a shaft 16.

Figure 2:
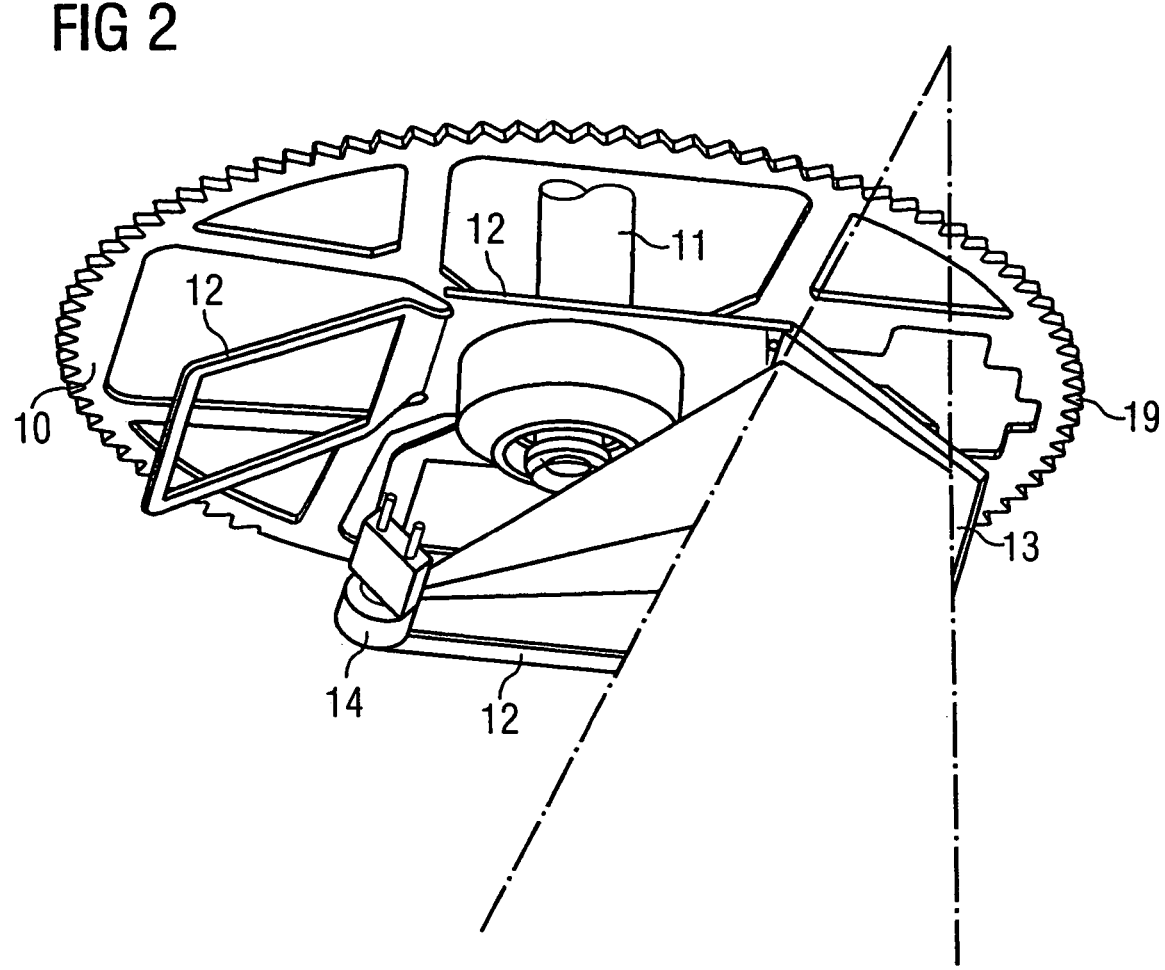
FIG. 2 is a perspective view of the basic components of the X-ray diagnostic device of FIG. 1.

FIG. 2 shows the disk 10 for the mirror 13 and the filters 12 as well as the lamp 9 in perspective. The disk 10 is formed as a sprocket with teeth 19. The spur gear 15 and the motor 17 and diaphragms 9 are not shown in FIG. 2.

Before a breast 18 that is supported on the subject table 5 is irradiated with X-rays for examination purposes, a light field is applied to the subject table 5, that is to say to the breast 18. For this purpose, the disk 10 is initially rotated into a position in which the mirror 13 is within the hypothetical X-ray path by the motor 17 and the spur gear 15. The lamp 9 is then turned on, whereby the light of the lamp 9 is reflected by the mirror such that the reflected light ray field reaches the subject table 5, that is to say the breast 18 that is being examined. A technician can now set the diaphragm plates 9 so that a desired X-ray field, i.e. a desired region of the breast that is to be exposed, can be established. The lamp 9 is then switched off. The disk 10 is then rotated by the motor 17 until one of the filters 12 whose function is to filter out undesirable X-radiation assumes the position previously occupied by the mirror 13, whereupon an X-ray exposure can be performed.

FIGS. 1 and 2 show that the filters are inclined relative to the disk 10. As a result, the path for the X-rays through the filter 12 is approximately the same length regardless of whether the rays in the X-ray field proceed perpendicular or at an angle to the examination subject.

The filters 12 on the disk 10 can be formed of various materials and can be various thicknesses and therefore exhibit different filter characteristics. The technician can select the appropriate filter 12 for the task, so that the subject receives an optimal X-ray dose in an X-ray imaging procedure.

The invention creates a combined filter and mirror mounting system with a minimum number of parts, so that the described positionings of the mirror and filters are simplified. The arrangement is relatively compact and thus can be contained in one diaphragm housing.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray diagnostic device comprising:

an X-ray tube that emits X-rays in an X-ray beam;

a diaphragm housing containing diaphragm plates movable relative to said X-ray beam for limiting an X-ray field produced by said X-ray beam;

a beam sighting arrangement including a lamp and a mirror disposed in said housing, said lamp emitting light that is reflected by said mirror for producing a light ray field substantially coinciding with a hypothetical X-ray field;

at least one filter disposed in said diaphragm housing for filtering the X-rays in said X-ray beam; and a single disk to which said filter and said mirror are mounted, said disk being rotatable around an axis of said disk for selectively moving either said mirror or said filter into said X-ray beam.

2. An X-ray diagnostic device as claimed in claim 1 wherein said disk is round and has a periphery, and comprising a plurality of teeth disposed at said periphery, and said X-ray diagnostic device comprising a motor-driven transmission interacting with said teeth at said periphery of said disk for rotating said disk.

* * * * *